United States Patent [19]
Balázs et al.

[11] Patent Number: 5,312,812
[45] Date of Patent: May 17, 1994

[54] PHARMACEUTICAL COMPOSITIONS COMPRISING NOVEL OLIGOPEPTIDES EXHIBITING SELECTIVE INHIBITING EFFECT UPON THE PROLIFERATION OF HEMOPOIETIC CELLS

[75] Inventors: András Balázs; István Schön; Tamás Szirtes, all of Budapest; Lajos Kisfaludy, deceased, late of Budapest, all of Hungary, by Andás Kisfaludy, Márta Kisfaludy, executors

[73] Assignee: Richter Gedeon Vegyeszeti Gyar Rt., Budapest, Hungary

[21] Appl. No.: 750,278

[22] Filed: May 17, 1994

[30] Foreign Application Priority Data

Sep. 3, 1990 [HU] Hungary .............................. 5745/90

[51] Int. Cl.$^5$ .............................................. A61K 37/00
[52] U.S. Cl. ........................................ 514/17; 514/18; 530/336; 530/330
[58] Field of Search .................... 514/17, 18; 530/336, 530/330; 564/102

[56] References Cited

U.S. PATENT DOCUMENTS 4,499,080  2/1985  Duffot et al. ........................ 514/12
4,987,122  1/1991  Laerum ................................ 514/15

FOREIGN PATENT DOCUMENTS 0359338  3/1990  European Pat. Off. .

*Primary Examiner*—Michael G. Wityshyn
*Assistant Examiner*—C. Sayala
*Attorney, Agent, or Firm*—Herbert Dubno; Jonathan Myers

[57] ABSTRACT

The present invention relates to novel peptides of formulae

Xaa Glu Asp Cys Lys            (SEQ I.D. No: 1), and

Glu Asp Cys Lys                (SEQ I.D. No: 2)

wherein the Cys sulfur is bonded to an acetamidomethyl group, and Xaa is pyro-Glu, the acid addition salts thereof, the pharmaceutical compositions comprising the same and a process for the preparation of the novel peptides and compositions.

The novel peptides selectively inhibit the proliferation of hemopoietic cells.

The invention also covers the treatment of mammals (including human beings) with the said peptides and compositions for selectively inhibiting the proliferation of hemopoietic cells.

The advantage of the novel compounds is that they are almost completely harmless, they do not have any side-effect in therapeutic dose-range, in addition they significantly inhibit the damaging effects of drugs and radiation used for the therapy of tumorous diseases or the dose of drug or radiation can be increased when they are administered.

2 Claims, No Drawings

PHARMACEUTICAL COMPOSITIONS COMPRISING NOVEL OLIGOPEPTIDES EXHIBITING SELECTIVE INHIBITING EFFECT UPON THE PROLIFERATION OF HEMOPOIETIC CELLS

TECHNICAL FIELD

The present invention relates to novel peptides of formulae

Xaa Glu Asp Cys Lys               (SEQ I.D. No: 1), and

Glu Asp Cys Lys                   (SEQ I.D. No: 2)

wherein Xaa is pyroglutamic acid and the Cys residue is S-substituted by an acetamidomethyl group (Acm), the acid-addition salts thereof, the pharmaceutical compositions comprising the same and a process for the preparation of the novel peptides and compositions.

The novel peptides selectively inhibit the proliferation of hemopoietic cells.

The invention also covers the treatment of mammals (including human beings) with the said peptides and compositions for selectively inhibiting the proliferation of hemopoietic cells.

BACKGROUND

Both oligopeptides are the analogues of the hemoregulating pentapeptide isolated from natural source. The isolation of a low molecular mass factor from a matured granulocytes and from the suspension of rat medulla (bone-marrow) was first described by Rytömaa and Kiviniemi. This factor inhibited the proliferation of myelopoietic rat cells in in vitro tests (Cell Tissue Kinet., 1, 329 and 341 (1968)).

Granulocyte chalon, as it was named at the beginning, turned out to slow down the proliferation in the S-phase of the cell cycle and to inhibit it in the $S_1$-phase (Virchows Arch. Abt. B. Zellpath., 14, 293 (1973)) while it inhibits the same in the $G_1$-phase of the cell cycle (In Vitro, 4, 47 (1969)).

The first homogenously purified myelopoietic inhibiting factor was described in Cell Biol. Intereact. Rep., 4, 337 (1980). This factor belongs to the nucleopeptides regarding the structure thereof. The isolation, approximate structure analysis and synthesis thereof was first reported in Z. Naturforsch., 37.c, 1297 (1982).

In 1986 it was declared that the synthetic Xaa Glu Asp Cys Lys where Xaa is pyroglutamic acid pentapeptide exhibits the same biological effects as the substance isolated from natural source (Biological Regulation of Cell Proliferation, edited by Basega, Foa, Netcalf and Polli, Raven Press, New York, 1986, page 11). This pentapeptide is SEQ I.D. No. 5.

So far the hemoregulating peptide has been isolated from human granulocytes, rat medulla and calf spleen. The myelopoiesis inhibiting effect thereof upon mouse, rat and human cells is dose-dependent in a concentration of higher than $10^{-13}$ mole/l. It has almost no side-effect. It is not toxic to human and mouse bone marrow cells in a concentration range of $10^{-15}$ to $10^{-4}$ mole/l in a 7-day in vitro treatment and to two mouse species in a dose of 9.1 mg/animal or 1 mg/animal (Pharmac. Ther., 44, 353 (1989)).

On the basis of the former facts it is not surprising that the hemoregulating peptide is considered as a future drug which will protect the bone marrow from the damage caused by cytostatic agents and radiation used for the treatment of tumorous diseases; however its use in other pharmaceutical fields may also be promising.

None of the few analogues synthesized so far has been found to exhibit similar biological activity. Several data indicate that the difficulties arising in the structural elucidation of the pentapeptide, consisting of only three-functional amino acids in addition to the amino-terminal pyroglutamic acid, the problems of the different synthesis routes and the deviation of the biological activity of the samples are in close relation with the susceptibility to decomposition of the compound due to its structure.

In Cancer Res., 50, 328 (1990), the authors cell the attention to the oxidative dimerization of the compound carrying a mercapto group and to its inactivation in aqueous solution under repeated freezing/melting. Its susceptibility to dimerization is especially disadvantageous as the activity of the dimer is the opposite of that of the monomer (Exp. Hematol., 12, 7. (1984); Exp. Hematol., 16, 274 (1988)).

No explanation is given in the article for the lack of activity of certain synthetic samples and inactivation. In our opinion these phenomena can at least partially be attributed to the ring-closure, isomerization and epimerization of compounds containing aspartic acid (J. Chem. Soc. Chem. Commun., 1983, 505; Acta Chim. Hung., 124, 919 (1987); Peptides 1986, editor: Theodoropulos, de Gruyter, Berlin, 1987, 83; Coll. Czech. Chem. Commun., 54, 3360 (1989)).

The opposite, i.e. cell proliferation stimulating effect of the dimer molecule Xaa Glu Asp Cys Lys Xaa Glu Asp Cys Lys and the ineffectiveness of Xaa Glu Asp Met Lys where Xaa is pyroglutamic acid (SEQ I.D. Nos: 3 and 4 respectively) on cell proliferation indicate that the mercapto group of cysteine has a significant role in eliciting the biological activity. The necessity of the presence of the mercapto group is supported by the fact that the natural SEQ I.D. No. 5 pentapeptide can inhibit the proliferation only in mercapto ethanol of 0.1 to 0.3 mmole/l, while without mercapto ethanol it is ineffective.

Among others, it is surprising that the SEQ I.D. No: 1 pentapeptide containing an acetamidomethyl group and the SEQ I.D. No: 2 tetrapeptide shortened at the amino-terminus, exhibit a significant and selective inhibiting effect upon the proliferation of myeloid cells.

The effect upon cell proliferation can be measured by several methods. The tests may measure e.g. the incorporation of tritiated thymidine into DNA in short-term cell (rat thymus and bone marrow cell) cultures or determine the colony-forming ability of mouse bone marrow cells in semi-solid agar culture.

DETAILED DESCRIPTION OF THE INVENTION

The compounds of the invention are subjected to the following tests:

Test on short-term culture

The rat bone marrow cells used for the short-term cultivation were isolated from two-week old rats weighing 40 g. After decapitating the animals, the femoral medulla was separated and suspended in so-called Parker medium "TC-199" (product of OKI) together with 10% fetal calf blood-serum (product of Gibco).

The samples taken from the suspension consisting of $3\times10^6$ cytoblastic medulla cells/ml were incubated per se (controls) in the presence of the test substances at 37° C. under an atmosphere comprising 5% by volume of carbon-dioxide saturated with vapour, for 4 hours, in blood-test tubes in a B 5060 EK Heraeus incubator.

In the third hour of incubation, 36 kBq/ml of $^3$H-Tdr tritiated thymidine (product of UWVR, Praha) of a specific activity of 721 MBq/ml was added.

60 minutes later $2\times100/\mu$l of aliquot samples were pipetted onto Whatman 3MM filter paper discs and the paper discs were washed subsequently with ice-cold 5% by weight perchloric acid solution, then ethanol and diethyl ether for 5 minutes, respectively, then dried.

The radioactivity of the paper discs was measured in a toluene-based mixture comprising 5 g/l of 2,5-diphenyl oxazole and 0.3 g/l of 1,4-bis(2-(5-phenyl)-oxazolyl)-benzene in a liquid scintillation spectrometer of Packard-TriCarb type. The number of the entries per minute was measured.

The number of entries of each sample was compared to that of the untreated control and expressed as the percentage of the untreated control.

According to the results in the presence of $10^{-7}$ mole/l the SEQ I.D. No: 5 pentapeptide and in the presence of $10^{-7}$ mole/l the SEQ I.D. No: 1 pentapeptide the incorporation of the tritiated thymidine into the cell culture decreased by 32% and 22%, respectively.

Test on long-term cell culture

For the long-term cultivation, cells isolated from mouse bone marrow were used in semi-solid agar culture.

$1.5\times10^5$ femoral medulla cells obtained from 2-3 month old male C57B1 mice were suspended in 1 ml of "McCoy 5A" medium (product of Gibco), then the following were added: 20% by volume of horse blood-serum (product of Gibco), 16% by volume of L-cell CSF (colony stimulating factor prepared from the supernatant of lymphocytes; product of the Pharmacological Institute of the Medical University of Debrecen, Hungary) and agar-agar to 0.18% by weight.

100 μl of the semi-solid medium were cultivated in a Micropet capillary for 7 days in the above-described manner, then the colonies were counted under a Zeiss-Cytoplast stereomicroscope of 40-times magnification.

The results are given as the percentage reduction of the numbers of colonies compared to the untreated control. The tests were carried out in the presence of 0.25 mmole/l mercapto ethanol (+ME) and without mercapto ethanol (−ME).

The results are summarized in the following table:

| Concentration ($10^{-x}$ mole/l) x | (A) (%) (+ME) | (1) (%) (+ME) | (1) (%) (−ME) | (2) (%) (−ME) |
| --- | --- | --- | --- | --- |
| 4 | 27 | 39 | 81 | — |
| 6 | 90 |    |    | 66 |
| 8 | 90 | 68 | 77 | 64 |
| 9 |    |    |    | 26 |
| 10 | 81 |   |    | 52 |
| 12 | 32 | 48 | 70 | 36 |
| 14 | 18 |    |    | 29 |

In the above table (A) represents the SEQ I.D. No.: 5 pentapeptide (1) stands for the SEQ I.D. No.: 1 pentapeptide while (2) is the SEQ I.D. No.: 2 tetrapeptide.

The cell cultures used in the thymidine test are of short life and the DNA-modification of only those cells are measured which are in the S-phase of the cell cycle in the fourth hour of the test (the cells receive the radioactive thymidine at that time). This portion is about 25 to 30% of the cells. The other cells are in phase $G_0$, $G_1$, $G_2$ or M.

Thus the inhibitions measured by the thymidine test are weaker than it can be achieved in the colony test. For example in the latter test the target cells are cultivated for 1 week after the treatment, thus the inhibitions can be accumulated or even reduce each-other.

The SEQ I.D. No.: 2 tetrapeptide, lacking pyroglutamic acid at the amino-terminus behaved in a very curious manner. While it inhibited the formation of semi-solid agar cultures by 25 to 65% in a concentration range of $10^{-14}$ to $10^{-6}$ mole/l, it did not inhibit the proliferation of either rat bone marrow or thymus cells on the basis of measuring the incorporation of tritiated thymidine.

The pentapeptide of formula (1), inhibiting both the incorporation of thymidine and the formation of colonies, influences the hemopoietic stem cells (CFUs) and has an influence upon the myeloid stem cells (CFUc) and to the myeloid precursor cells, myeloblasts, promyelocytes and myelocytes.

The tetrapeptide of formula (2) does not have any effect upon the latter cells, however it inhibits the proliferation of colony-forming, myeloid stem cells (CFUc) with an especially high selectivity, i.e. it is both of cell line and compartment specificity.

In a $^{51}$Cr-emission test carried out with crtoblastic bone marrow cells, reflecting the in vitro toxicity of the compounds, both peptides of the invention proved to be non-toxic.

In order to measure the in vivo activity, the compounds were administered intraperitoneally to rats weighting 40 g. A 40 percentage reduction of the medulla mitosis compared to the control was observed, thus the in vivo inhibition of proliferation can also be considered as significant.

The presence of the acetamidomethyl group is advantageous not only from the point of view of biological activity, but from chemical point of view, too, as it eliminates the frequent instability of the molecule carrying a free mercapto group and the significant deviation of the biological test results, partially attributed to the instability.

As far as we know these are the first biologically active mercapto compounds which comprise an Acm-group. Their special advantage is that they are hardly susceptible to oxidation under air compared to the compounds carrying a free mercapto group, thus they are much more stable and can be stored longer under normal conditions.

A further advantage of the oligopeptides of formulae (1) and (2) of the invention is that they can be prepared by a relatively simple synthesis in solution or in solid phase contrary to the high molecular polypeptides exhibiting similar activity (Nature, 344, 442 (1990)).

The peptides having SEQ I.D. Nos: 1 and 2 are prepared according to the invention by
 step-wise chain-lengthening of the protected intermediates of the peptides of formulae (1) and (2), starting from the C-terminal amino acid derivative, using successively active ester coupling and base catalyzed liberation of the alpha-amino group, while blocking the non-reacting amino and carboxyl functions by groups removable with mild acidolysis and protecting the mercapto group of cysteine residue with an acetamidomethyl group, then deblocking these protected intermediates by mild acidolysis, and, if desired, converting the free oligopeptides of formulae (1) and (2) into their acid-addition salts.

In the course of the synthesis such combination of protective groups is used which enables the selective removal of the amino-protective group, then at the end of the synthesis, the removal of all acid-sensitive protective groups possibly in one step.

The peptide-bond is formed by the active ester, preferably by the pentafluorophenyl ester (—OPfp) method (Synthesis, 1983, 325).

For the transistional protection of the alpha-amino groups to be subsequently built into a peptide bond, the 9-fluorenylmethyl-oxy-carbonyl group (Fmoc), cleavable with a base, is preferably used. The $\epsilon$-amino group of lysine, the amino group of glutamic acid of oligopeptide of formula (2) and optionally the amide-nitrogen of the pyroglutamic acid of oligopeptide of formula (1) are preferably protected by t-butoxycarbonyl (Boc-) group. For the protection of the non-activated carboxyl groups in the side-chains and at the carboxyl terminus, preferably the esterification with t-butanol is used.

From the protected peptides prepared as described hereinabove, the protective groups except the S-acetamidomethyl group are removed, then the oligopeptide thus obtained is optionally transformed into an acid-addition salt with the aid of an anion-cycle anion-exchange resin suitable for the salt formation.

The peptides thus obtained are of pharmaceutical purity, they do not need further purification. In case of necessity they can be purified on a silica gel column or with highly effective liquid chromatography.

The peptide obtained in the form of a solution can be recovered by evaporating or freeze-drying the solution. The free peptide can be transformed into a salt in the above-described manner, preferably it is transformed into a pharmaceutically acceptable acid-addition salt. Such salts are e.g. the salts formed with hydrochloric, sulfuric, phosphoric, acetic, citric, maleinic or amygdalic acid.

The peptides of the present invention and the acid-addition salts thereof can be used in the form of usual pharmaceutical compositions as adjuvants in the therapy of tumorous diseases.

The advantage of the novel compounds is that they are almost completely harmless, they do not have any side-effect in the therapeutic dose-range, in addition they significantly inhibit the damaging effects of drugs and radiation used for the therapy of tumorous diseases or the dose of drug or radiation can be increased when they are administered.

The peptides of formulae (1) and (2) can be administered per se or in the form of salts, preferably in pharmaceutically conventional forms, e.g. solid, liquid or semisolid forms.

When the compositions are prepared, the usual carriers, diluents, stabilizing, pH adjusting, osmotic pressure adjusting, formulation enabling or facilitating additives and excipients can be used.

The solid pharmaceutical compositions may for example be powder ampoules for injections. The liquid compositions are the injectables, infusions including the microcapsules.

The patient is administered with the pharmaceutical composition comprising the desired dose of drug. This dose depends on the degree of disease, the body weight of the recipient, the route of administration, the number of daily treatments and the method of other treatments. The suitable dose can be determined by the physician in the knowledge of the patient to be treated.

In order to simplify the administration, it is preferable to prepare dose-units comprising one dose or the multiple or half, third, quarter of one dose of the drug administered.

The pharmaceutical compositions according to the invention generally comprise 1 to 250 mg of active ingredient in one dose-unit. Certainly the amount of the active ingredient may exceed the formerly defined upper or lower limits.

The invention is illustrated in detail by the following, non-limiting working examples.

The abbreviations used in the description correspond to the generally accepted abbreviations (Biochem. J., 219, 345 (1984)). All of the amino acids are of L-configuration, therefore it is not indicated separately.

In the amino acid analysis following the examples, "Tin" means 4-thiazolidine carboxylic acid formed during the hydrolysis of S-acetamidomethyl cysteine.

The melting points were determined in a dr. Tottoli apparatus (Büchi, Switzerland).

The thin-layer chromatographic tests were carried out on ready-made silica gel adsorbent (DC-Fertigplatten, Merck, Germany) with the following solvent mixtures (the ratios mean volume ratios):

"stock solution":20:6:11 mixture of pyridine/acetic acid/water 1) 99:1 mixture of ethyl acetate/stock solution
2) 19:5 mixture of ethyl acetate/stock solution
3) 9:1 mixture of ethyl acetate/stock solution
4) 4:1 mixture of ethyl acetate/stock solution
5) 2:3 mixture of ethyl acetate/stock solution
6) 1:4 mixture of ethyl acetate/stock solution
7) 3:7 mixture of n-butanol/stock solution
8) 1:1:1:1 mixture of n-butanol/acetic acid/ethyl acetate/water The chromatograms were developed with ninhydrine and potassium iodide/tolidine after chlorination.

The high pressure liquid chromatographic measurements were carried out in an equipment supplied with a Labor-MIM 300 type UV detector of variable wavelength, a Labor-MIM loop-injector, a feeding pump and manometer consisting of Gilson 8020 and 302 units and recorder of Radelkis OH-827 type.

The separation was carried out on a 150 cm long column filled with $C_{18}$ phase (Labor MIM) of 10 /$\mu$m particle size, having an external diameter of 4.6 mm. The eluent comprised 97 parts by volume of water, 3 parts by volume of acetonitrile and 0.4 parts by volume of trifluoroacetic acid. The measurements were carried out with a flow rate of 1 ml/minute, the light absorption of the solution was detected at 220 nm.

The purity of the peptides exceeded the 95% on the basis of both the thin-layer chromatographic and liquid chromatographic methods.

The specific rotation was measured in a polarimeter of Perkin-Elmer 241 type. The solvents were removed and the evaporations were carried out in a rotating vacuum evaporator over a water-bath of up to 40° C. in all cases.

The amino acid analysis of the target compounds was carried out in a Biotronik LC 5001 apparatus. The samples were hydrolyzed in 6 moles/l of hydrochloric acid solution at 110° C. for 24 hours. The results of the analysis were within the ±5% error. In the course of hydrolysis the main part of S-acetamidomethyl cystein transformed into 4-thiazolidine carboxylic acid (Tin).

EXAMPLE 1

SEQ I.D. No.: 2 Tetrapeptide 5.81 g (10 mmoles) of Fmoc-Cys-(Acm)-OPfp and 3.54 g (10.5 mmoles) H-Lys(Boc)-O$^t$Bu.HCl are reacted in 20 ml of dimethyl formamide in the presence of 1.47 ml (10.5 mmoles) of triethyl amine. 4 hours later the reaction mixture is diluted with 100 ml of ethyl acetate and the mixture thus obtained is washed with 50 ml of water, 3×30 ml of 1 mole/l aqueous hydrochloric acid solution, 3×30 ml of 5% aqueous sodium hydrocarbonate solution, dried over anhydrous sodium sulfate and evaporated in vacuum.

The oil obtained as evaporation residue is dissolved in 15 ml of ethyl acetate under heating and the solution is diluted with 60 ml of n-hexane. The suspension is kept cold for a night, then filtered and the precipitate is washed with n-hexane.

Thus 4.4 g (63% calculated for the active ester) of Fmoc-Cys(Acm)-Lys(Boc)-O$^t$Bu are obtained.

Melting point: 110°–113° C.
$(\alpha)^{D}_{20}$: −22.8° (c=1.0, in ethanol)
$R_f2$: 0.60.

1.6 g (2.29 mmoles) of the above dipeptide are treated with 15 ml of dimethyl formamide containing 10% of dimethyl amine, then the reaction mixture is evaporated in vacuum, n-hexane in several portions is poured onto the oily residue, then the supernatant is decanted, finally the precipitate is dissolved in 10 ml of dimethyl formamide.

To the solution 1.5 g (2.6 mmoles) of Fmoc-Asp(O$^t$-Bu)-OPfp are added, 1 hour later the reaction mixture is evaporated in vacuo, n-hexane is poured several times onto the oil obtained as evaporation residue, then the supernatant is decanted, finally crystallized by the addition of diisopropyl ether.

Thus 1.52 g (76.1%) of Fmoc-Asp(O$^t$Bu)-Cys(Acm)-Lys(Boc)-O$^t$Bu are obtained. A small sample is recrystallized from ethyl acetate. The physical characteristics of this sample are as follows:

Melting point: 124°–125° C.
$(\alpha)^{D}_{20}$: −31.8° (c=1.0, in ethanol)
$R_f3$: 0.70.

1.4 g (1.61 mmoles) of tripeptide obtained as described hereinabove are treated with dimethyl formamide containing 10% of dimethyl amine as described in the former paragraph. To the oil obtained as residue after the evaporation of the reaction mixture, n-hexane is poured several times, then the supernatant is decanted, finally dissolved in 6 ml of dimethyl formamide and reacted with 0.83 g (1.75 mmoles) of Boc-Glu(O$^t$-Bu)-OPfp.

1.5 hours later the reaction mixture is evaporated, the residue is subjected to chromatography on a column prepared form 30 ml of silica gel by using mixture No. 1 for the elution. The pure fractions are collected, evaporated in vacuum, the oil obtained as evaporation residue is solidified in the mixture of diisopropyl ether and n-hexane.

Thus 1.22 g (81.3%) of amorphous Glu-Asp-Cys-Lys (SEQ. I.D. No: 6) are obtained where the beta-Asp, gamma-Glu and C-terminal COOHs are blocked by t-butyl, the N-terminal and Lys epsilon amino groups are blocked by Boc and the lys S is bonded to an Acm group.

$(\alpha)^{D}_{20}$: −42.2° (c=1.0, in ethanol)
$R_f2$: 0.45.

1.15 g (1.24 mmoles) of of protected tetrapeptide obtained as described hereinabove are treated with 25 ml of 4 moles/l hydrogen chloride in acetic acid solution. 30 minutes later the supernatant is discharged, ether is poured onto the residual oil, the supernatant is decanted, dissolved in 15 ml of water and treated with Dowex 2-x 8 anion exchange resin of acetate cycle.

The solution is evaporated in vacuum and the residue is isolated with ethanol. The crude product is chromatographed on a column prepared from 30 g of silica gel by using mixture No. 5 as eluent. The pure fractions are collected, evaporated and the residue is recrystallized from a mixture of water and ethanol.

Thus 0.28 g (40.0%) of amorphous SEQ. I.D. No: 2 tetrapeptide are obtained which contains 2–3% of Xaa Asp Cys Lys as contaminant (SEQ. I.D. No: 7 where Xaa is pyro-Glu and the Cys S is bonded to an Acm group.

$(\alpha)^{D}_{20}$: −33.7° (c=0.6, in water)
$R_f6$: 0.35;
$R_f8$: 0.25.
Amino acid analysis:

| Lys = 0.92 (1), | Asp = 1.04 (1), | Glu = 1.04 (1), |
| Cys = 0.36 (1), | Tin = 0.32, | NH$_3$ = 0.63. |

EXAMPLE 2

(SEQ. I.D. No: 1 Pentapeptide 4.5 g (5.17 mmoles) of Fmoc-Asp(O$^t$Bu)-Cys(Acm)-Lys(Boc)-O$^t$Bu are treated with 40 ml of dimethyl formamide containing 10% of dimethyl amine. 10 minutes later the reaction mixture is evaporated in vacuum, n-hexane is poured onto the residue several times, then the supernatant is decanted. The solid substance is dissolved in 20 ml of dimethyl formamide and reacted with 3.55 g (6.0 mmoles) of Fmoc-Glu(O$^t$Bu)-OPfp.

1 hour later the reaction mixture is evaporated, the residue is dissolved in 10 ml of ethyl acetate, then the solution is diluted with 50 ml of diisopropyl ether. Next day the suspension is filtered off.

Thus 4.46 g (81.8%) of Glu Asp Cys Lys (SEQ I.D. No. 8) obtained where the beta-Asp, gamma-Glu and C terminal COOHs are blocked by t-butyl, the N-terminal is blocked by Fmoc, the Lys epsilon amino is blocked by Boc and the Cys S is bonded to an Acm group.

Melting point: 111°–115° C.
$(\alpha)^{D}_{20}$: −38.4° (c=1.0, in ethanol)
$R_f2$: 0.70;
$R_f4$: 0.90.

1.60 g (1.52 mmoles) of above protected tetrapeptide are treated with 15 ml of dimethyl formamide containing 10% of dimethyl amine, then the reaction mixture is evaporated in vacuum and n-hexane is poured several times onto the oil obtained as evaporation residue, then the supernatant is decanted. The free tetrapeptide thus obtained ($R_f4$=0.35) is dissolved in 8 ml of dimethyl formamide and reacted with 0.59 g (2.0 mmoles) of Glu-OPfp. 1 hour later the reaction mixture is evaporated and the residue is isolated with ether.

Thus 1.0 g (69.7%) of Xaa Glu Asp Cys Lys (SEQ. I.D. No. 9); are obtained where Xaa is pyro-Glu, the beta-Asp, gamma-Glu and C-terminal COOHs are blocked by t-butyl, the Lys epsilon amino is blocked by Boc, and the Cys S is bonded to an Acm group.

Melting point: 158°–160° C.
$(\alpha)^D_{20}$: −42.7° (c=1.0, in ethanol)
$R_fA$: 0.55.

0.90 g (0.95 mmole) of the above protected tetrapeptide is treated with 10 ml of 4 moles/1 hydrogen chloride in acetic acid solution for 30 minutes, then the supernatant is discharged and the residue is isolated with ether.

The crude product is chromatographed on a column prepared from 20 g of silica gel by using mixture No. 8 as eluent. The pure fractions are collected, evaporated, then the residue is precipitated from a mixture of ethanol and ethyl acetate then from a mixture of methanol and ethyl acetate.

Thus 0.33 g (51.4%) of the SEQ. I.D. No. 1 Pentapeptide pentapeptide are obtained.

$(\alpha)^D_{20}$ : −22.8° (c=1.0, in ethanol)
$R_f7$: 0.35.
Amino acid analysis:

| Lys = 1.0 (1), | Asp = 0.98 (1), | Glu = 2.03 (1), |
|---|---|---|
| Cys = 0.31 (1), | Tin = 0.45 | NH$_3$ = 0.72. |

EXAMPLE 3

SEQ. I.D. No.: 1 Pentapeptide 2.90 g (2.75 mmoles) of the SEQ. I.D. No. 8 tetrapeptide are treated with 25 ml of dimethyl formamide containing 10% of dimethyl amine. 10 minutes later the reaction mixture is evaporated, n-hexane is poured several times onto the oil obtained as evaporation residue, then the suspension is decanted. The solid substance is dissolved in 15 ml of dimethyl formamide and reacted with 1.30 g (3.3 mmoles) of BocGlp-OPfp. 1 hour later the reaction mixture is evaporated, the residue is isolated with diisopropyl ether.

Thus 2.62 g (91.2%) of Xaa Glu Asp Cys Lys (SEQ I.D. No: 10) are obtained where Xaa is pyro-Glu, the beta Asp, Gamma-Glu and C terminal COOHs are blocked by t-butyl, the N terminal and Lys epsilon amino groups are blocked by Boc and the Cys S is bonded to an Acm group.

Melting point: 96°–101° C.
$(\alpha)^D_{20}$: −47.0° (c=1.0, in methanol)
$R_f5$: 0.40.

2.50 g (2.39 mmoles) of the above protected pentapeptide are treated with a mixture of 40 ml of trifluoroacetic acid and 5 ml of anisole for 2 hours at room temperature. The reaction mixture is evaporated to a volume of 10 ml, then the residue is diluted with ether. The suspension is filtered off, the precipitate is thoroughly washed with ether, then dissolved in 30 ml of water after drying.

The solution is treated with 10 ml of Dowex 2x 8 anion exchange resin of acetate cycle, then the resin is filtered off and the filtrate is evaporated in vacuum. The residue is recrystallized from a mixture of ether and methanol.

Thus 0.95 g (58.8%) of pentapeptide of SEQ I.D. No: 1 are obtained.

$(\alpha)^D_{20}$: −53.7° (c=1.0, in methanol)

EXAMPLE 4

Injectable powder ampoule 500 mg of the SEQ I.D. No: 1 pentapeptide and 9.5 g of lactose are dissolved in 80 ml of distilled water, suitable for the preparation of injections, 0.1 g of methyl p-hydroxy benzoate is added, then the volume of the solution is supplemented to 100 ml with distilled water suitable for the preparation of injections. The homogeneous solution is filtered to sterile, each 1 ml is filled into vials, freeze-dried then the vials are closed with a polymeric stopper.

Thus powder ampoules comprising 5 mg of active ingredient are obtained.

When the active ingredient content of the powder ampoule is different from the above one, the amount of lactose is preferably choosen in such a manner that the total amount of lactose and the active ingredient should be about 10 g calculated to 100 ml of solution. Instead of lactose, the same amount of mannitol may also be used.

When the drug is administered, the powder is dissolved in such an amount of aqueous sodium chloride solution which enables the preparation of an isotonic solution.

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /label=Seq1
            / note="Xaa is pyroglutamic acid and an
            acetamidomethyl group (Acm) is bonded to the Cys
            sulfur."

( x i ) SEQUENCE DESCRIPTION: SEQ ID NO:1:

Xaa Glu Asp Cys Lys
1                 5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /label=Seq2
            / note="The Cys sulfur atom is bonded to an Acm moiety."

( x i ) SEQUENCE DESCRIPTION: SEQ ID NO:2:

Glu Asp Cys Lys
1

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=Seq3
            / note="The Xaa in positions 1 and 6 is pyroglutamic acid and this peptide is a dimer."

( x i ) SEQUENCE DESCRIPTION: SEQ ID NO:3:

Xaa Glu Asp Cys Lys Xaa Glu Asp Cys Lys
1                 5                 10

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /label=Seq4
            / note="Xaa is pyroglutamic acid."

( x i ) SEQUENCE DESCRIPTION: SEQ ID NO:4:

Xaa Glu Asp Met Lys
1                 5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide (B) LOCATION: 1..5
            (D) OTHER INFORMATION: /label=Seq5
                    / note="Xaa is pyroglutamic acid."

(xi) SEQUENCE DESCRIPTION: SEQ ID NO:5:

Xaa  Glu  Asp  Cys  Lys
    1                    5

(2) INFORMATION FOR SEQ ID NO:6:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /label=Seq6
                    / note="The N-terminal of Glu and the
                    epsilon- amino of Lys are blocked by Boc, the
                    beta-Asp, gamma-Glu and C-terminal COOHs are (xi) SEQUENCE DESCRIPTION: SEQ ID NO:6:

Glu  Asp  Cys  Lys
    1

(2) INFORMATION FOR SEQ ID NO:7:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /label=Seq7
                    / note="Xaa is pyroglutamic acid and the sulfur
                    atom of the Cys is bonded to an Acm group."

(xi) SEQUENCE DESCRIPTION: SEQ ID NO:7:

Xaa  Asp  Cys  Lys
    1

(2) INFORMATION FOR SEQ ID NO:8:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /label=Seq8
                    / note="The beta-Asp, gamma-Glu, & C terminal
                    COOHs are blocked by t-butyl, the N-terminal amino
                    is blocked by Fmoc,the epsilon-amino of Lys is (xi) SEQUENCE DESCRIPTION: SEQ ID NO:8:

Glu  Asp  Cys  Lys
    1

(2) INFORMATION FOR SEQ ID NO:9:

(i) SEQUENCE CHARACTERISTICS:
            (A) LENGTH: 5 amino acids (B) TYPE: amino acid
(D) TOPOLOGY: linear (ii) MOLECULE TYPE: peptide (ix) FEATURE:
(A) NAME/KEY: Peptide
(B) LOCATION: 1..5
(D) OTHER INFORMATION: /label=Seq9
/ note="Xaa is pyro-Glu, the beta-Asp, gamma-Glu,
and C terminal COOHs are blocked by t-butyl, the
Cys S is bonded to Acm, and the epsilon amino of (xi) SEQUENCE DESCRIPTION: SEQ ID NO:9:

Xaa Glu Asp Cys Lys
1                 5

(2) INFORMATION FOR SEQ ID NO:10:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Peptide
(B) LOCATION: 1..5
(D) OTHER INFORMATION: /label=Seq10
/ note="Xaa is pyro-Glu, the beta-Asp, gamma-Glu &
C-terminal COOHs are blocked by t-butyl, the Cys S
is bonded to Acm, and the N-terminal & epsilon (xi) SEQUENCE DESCRIPTION: SEQ ID NO:10:

Xaa Glu Asp Cys Lys
1                 5

We claim:

1. A pharmaceutical composition for selectively inhibiting the proliferation of hemopoietic cells, which comprises a therapeutically effective amount of a peptide selected from the group consisting of Xaa Glu Asp Cys Lys          (SEQ I.D. No. 1)

and

Glu Asp Cys Lys              (SEQ I.D. No: 2)

where Xaa is pyroglutamic acid and the Cys residue is bonded to an acetamidomethyl group, or a pharmaceutically acceptable acid addition salt thereof, in combination with a pharmaceutically acceptable inert carrier.

2. A method for the selective inhibition of the proliferation of hemopoietic cells in a mammalian subject which comprises administering to said mammalian subject a therapeutically effective amount of the pharmaceutical composition defined in claim 1.

* * * * *